United States Patent [19]

Clayman et al.

[11] Patent Number: 4,629,461

[45] Date of Patent: Dec. 16, 1986

[54] POSTERIOR CHAMBER INTRA-OCULAR LENS

[76] Inventors: Henry Clayman, 12555 Biscayne Blvd., Miami, Fla. 33181; James R. Longacre, 3621 Littledale Rd., Kensington, Md. 20895

[21] Appl. No.: 668,151

[22] Filed: Nov. 5, 1984

[51] Int. Cl.⁴ .................................. A61F 2/16
[52] U.S. Cl. ............................................ 623/6
[58] Field of Search ................................. 3/13; 623/6

[56] References Cited

U.S. PATENT DOCUMENTS

| Re. 31,626 | 7/1984 | Hoffer | 3/13 |
|---|---|---|---|
| 4,073,014 | 2/1978 | Poler | 3/13 |
| 4,080,709 | 3/1978 | Poler | 3/13 X |
| 4,118,808 | 10/1978 | Poler | 3/13 |
| 4,122,556 | 10/1978 | Poler | 3/13 |
| 4,149,279 | 4/1979 | Poler | 3/13 |
| 4,159,546 | 7/1979 | Shearing | 623/6 |
| 4,244,060 | 1/1981 | Hoffer | 3/13 |
| 4,249,271 | 2/1981 | Poler | 3/13 |
| 4,249,272 | 2/1981 | Poler | 3/13 |
| 4,270,230 | 6/1981 | Poler | 3/13 |
| 4,277,852 | 7/1981 | Poler | 3/13 |
| 4,298,994 | 11/1981 | Clayman | 3/13 |
| 4,298,995 | 11/1981 | Poler | 3/13 |
| 4,315,336 | 4/1982 | Poler | 3/13 |
| 4,326,306 | 4/1982 | Poler | 3/13 |
| 4,327,171 | 4/1982 | Poler | 430/323 |
| 4,377,329 | 3/1983 | Poler | 351/160 R |
| 4,402,579 | 9/1983 | Poler | 3/13 X |
| 4,434,515 | 3/1984 | Poler | 3/13 |
| 4,435,050 | 3/1984 | Poler | 3/13 X |
| 4,439,873 | 4/1984 | Poler | 3/13 |
| 4,450,593 | 5/1984 | Poler | 3/13 |
| 4,466,858 | 8/1984 | Poler | 156/643 |
| 4,473,434 | 9/1984 | Poler | 156/630 |
| 4,485,499 | 12/1984 | Castleman | 3/13 |
| 4,495,665 | 1/1985 | Kelman | 3/13 |
| 4,547,914 | 10/1985 | Castleman | 623/6 |
| 4,547,915 | 10/1985 | Castleman | 623/6 |
| 4,562,600 | 1/1986 | Ginsberg et al. | 623/6 |

FOREIGN PATENT DOCUMENTS 2124500 2/1984 United Kingdom ...................... 3/13

Primary Examiner—Ronald L. Frinks
Attorney, Agent, or Firm—Cushman, Darby & Cushman

[57] ABSTRACT

A posterior chamber intra-ocular lens with a plurality of separated protrusions extending rearwardly from the lens to separate the optical portion from the posterior capsule. The protrusions may be integral with the lens body or formed as a separate element. The protrusions may be fixed in bore holes or mounted in a ring. Material more flexible and softer than the lens body such as silicone or HEMA can be used for the protrusions.

15 Claims, 8 Drawing Figures

FIG. 6
FIG. 7
FIG. 8
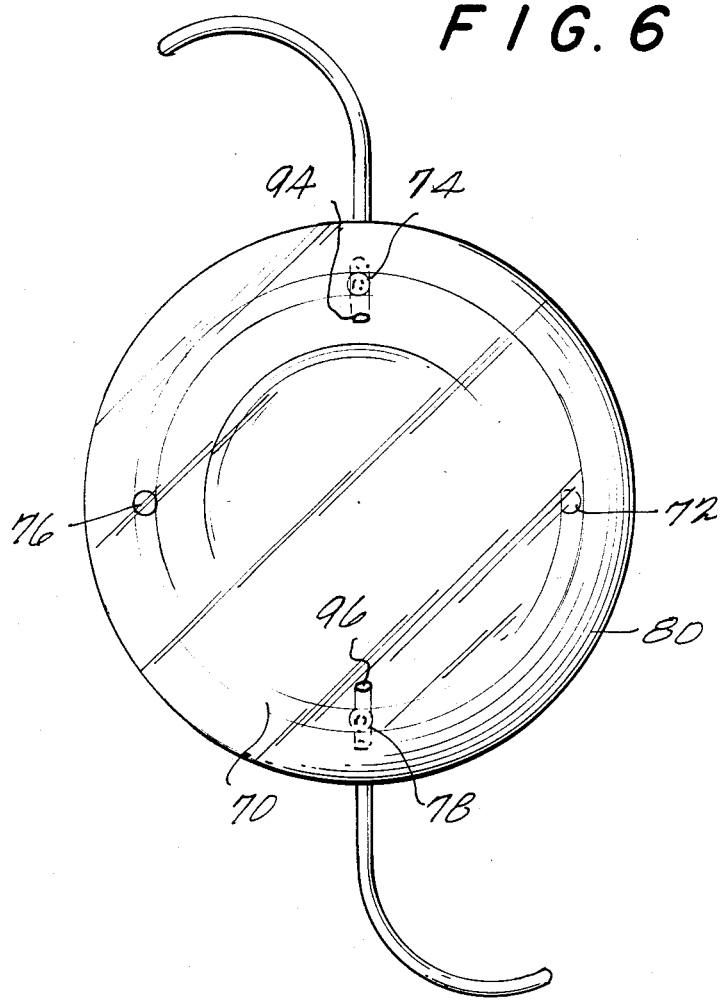
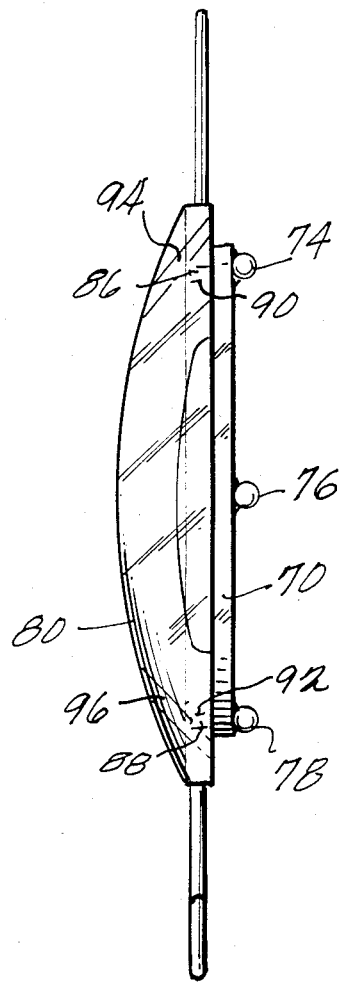
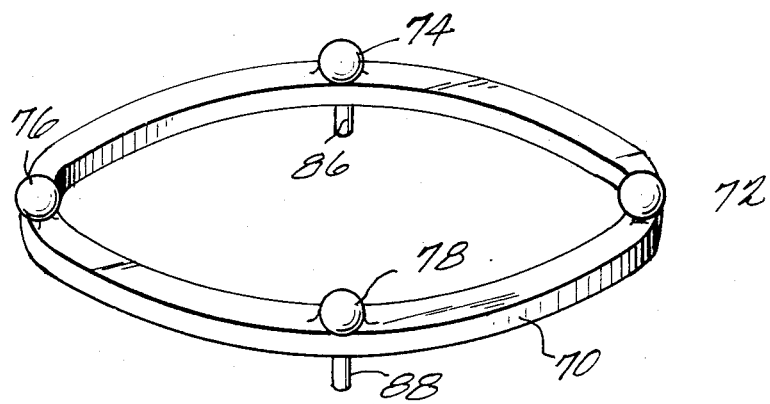

POSTERIOR CHAMBER INTRA-OCULAR LENS

BACKGROUND AND SUMMARY OF THE INVENTION

The invention relates to an improved posterior chamber intra-ocular lens designed for implantation in the eye.

Surgical removal of opaque lenses from the eyes of cataract patients is one of the most common surgical procedures. In the past, contact lenses or spectacles were usually prescribed for the patient to provide at least limited vision following the operation. The optical and other drawbacks of contact lenses and spectacles for such purpose were numerous. Today implantation of an artificial intra-ocular lens to replace the removed opaque natural lens is the preferred way to restore the patients sight.

The natural lens in the eye serves to focus the light entering the eye through the cornea onto the retina. The lens is surrounded by a thin capsule. In cataract surgery either the entire lens, including the capsule, is removed intact in a so called intracapsular extraction or the transparent rear wall of the capsule (the so called posterior capsule) is left in the eye in the so called extracapsular cataract extraction. Extracapsular extraction is now the preferred technique.

The eye is divided by the iris into an anterior chamber in front of the iris and a posterior chamber behind the iris. The implant can be placed either in the anterior chamber or the posterior chamber. Placement in the posterior chamber is now preferred for a number of reasons.

One of the particular advantages of placement in the posterior chamber is that the implant need not be sutured to the eye and can simply be positioned by the use of centering loops or the like extending from the lens body. U.S. Pat. Nos. 4,159,546 and 4,298,994 describe implants of this type designed for implantation in the posterior chamber.

Typically the rear surface of an intra-ocular lens implanted in the posterior chamber contacts the posterior capsule over at least a substantial portion of its surface. This may to some extent impede natural flow of fluids, possibly resulting in some damage to the posterior capsule. The rear surface of the lens can also to some extent abrade the posterior capsule and possibly damage that capsule.

In a small percentage of cases the naturally transparent posterior capsule becomes cloudy following implantation. In this instance the capsule must be opened so that light can be focused onto the retina. Until recently this was normally accomplished by inserting an instrument into the eye to cut through the posterior capsule, i.e., a so called discission. However, this operation is now very easily accomplished on an outpatient basis by the use of a Neodynium YAG laser. The coherent light from the laser is focused directly on the posterior capsule to in effect form a hole in the capsule without any damage to other portions of the eye.

However, if the rear surface of an implant is in contact or closely adjacent the spot on which the laser is focused, that portion of the lens will also be damaged by the laser resulting in a mark on the lens which will appear in the field of vision of the patient.

The patent to Hoffer U.S. Pat. No. 31,626 describes an intra-ocular lens designed for implantation in the posterior chamber and in which an annular lip or ridge is provided on the rear surface of the lens for spacing that surface from the posterior capsule. This is said to facilitate discission by permitting an instrument to be inserted behind the lens and also to discourage or eliminate growth of lens material subsequent to extra capsular extraction.

The present invention relates to an improved intra-ocular lens in which the rear surface of the lens body is provided with a plurality of separated protrusions extending outwardly and rearwardly from the optical portion of the lens to contact the posterior capsule and separate the posterior capsule from the rest of the lens body. This ensures that the optical portion of the lens will not be marked during any operation with a YAG laser. Moreover the protrusions contact only a small area of the posterior capsule minimizing any possible damage to this delicate structure. Fluids can easily circulate between the optical portion of the lens and the posterior capsule and such fluid circulation is not in any way blocked by an annular extended ridge, lip or other structure. In lenses which have an annular lip should the lip after implantation fall into the pupil the distortion will be great. Similarly the lip causes distortion in the field of view of a surgeon who has to repair retinal detachment subsequent to implantation. The use of protrusions avoids both these difficulties. As in other lenses of this type, appendages, for example haptic loops or the like, extend from the lens body for positioning the lens within the eye after implantation.

In a first embodiment of the present invention the protrusions are an integral part of the lens body and are disposed about a central optical portion. The appendages which position the lens body are also an integral portion of the lens body.

In a second embodiment of the present invention the protrusions are fixed to the lens body in bore holes which are drilled in the rear surface during manufacture. Conventionally, one or two such bore holes are provided through the lens for facilitating insertion during the surgical procedures so drilling additional holes does not substantially complicate manufacture.

Utilizing protrusions which are separate from the lens body permits the protrusions to be of a different material which may be more friendly to the eye. It may be desirable to utilize material such as silcone or hydroxy ethyl methacrylate (HEMA) commonly known as "soft lens" material which is softer than the polymethylmethacrylate now conventionally used as the material for the lens body. Both materials are compatible with eye tissue.

In addition, utilizing separate protrusions enables the surgeon or the manufacturer to very readily adapt any given lens to select any desired material, size of protrusion or number of protrusions. The protrusions may be in the form of a ring which is anchored at one or more locations to a bore hole with separated protrusions extending outwardly therefrom.

Other objects and purposes of the invention will be clear from the following detailed description of the drawings.

BRIEF DESCRIPTION OF THE DRAWINGS

FIG. 6 shows a front view of a variation of the second embodiment of the invention in which the protrusions are disposed on a ring anchored to the rear surface of the lens body.

FIG. 7 shows a side view of the arrangement of FIG. 6.

FIG. 8 shows a perspective view of the ring with its feet and protrusions.

DETAILED DESCRIPTION OF THE DRAWINGS

Figure 1:
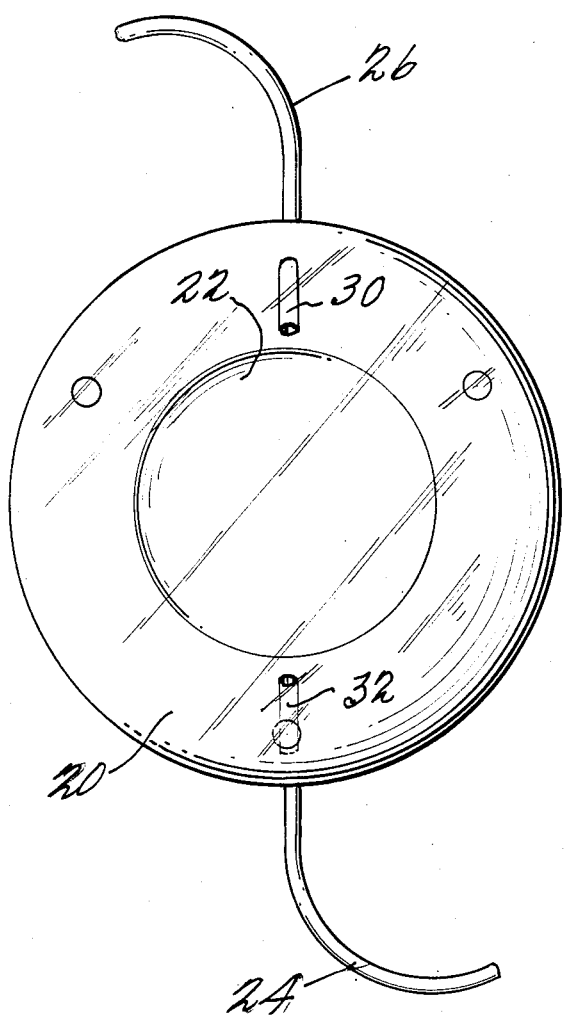
FIG. 1 shows a front view of a first embodiment of the present invention with integral protrusions extending from the rear surface of the lens body.
Figure 2:
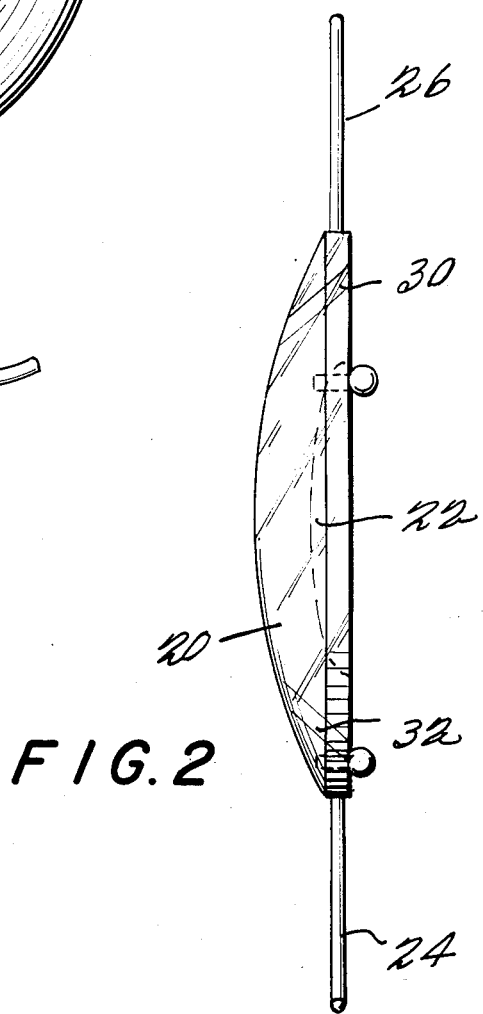
FIG. 2 shows a side elevation view of the lens of FIG. 1.

Reference is now made to FIGS. 1 and 2 which illustrate a first embodiment of the present invention. The lens includes a lens body 20 with a central optical portion 22 which when implanted serves the same function of the natural lens of the eye. Haptic loops 24 and 26 conventionally extend oppositely from the lens body and are integral with that body. The loops 24 and 26 are formed by cutting, casting, extrusion molding or a combination thereof. of a Although the appendages 24 and 26 are termed haptic loops they need not be curved and can be of any shape suitable for fixing the lens in the capsular bag or siliary sulcus. If desirable more than two such appendages can be provided.

A plurality of integral protuberances extending rearwardly and outwardly from the rear surface of lens body 20 are provided thereon about the periphery of optical portion 22. Three or four protrusions are believed sufficient but any desired number can be provided. These protuberances are formed during manufacture. Preferably the protuberances are smooth as shown in FIG. 2 and extend outwardly between 0.1 and 1 millimeter and more preferably between 0.2 and 0.5 millimeter. This distance provides adequate spacing of the rear surface of the lens body from the posterior capsule without substantially interfering with surgical insertion. As can be best seen in FIG. 2, bore holes 30 and 32 are provided for facilitating insertion of the lens implant.

Figure 3:
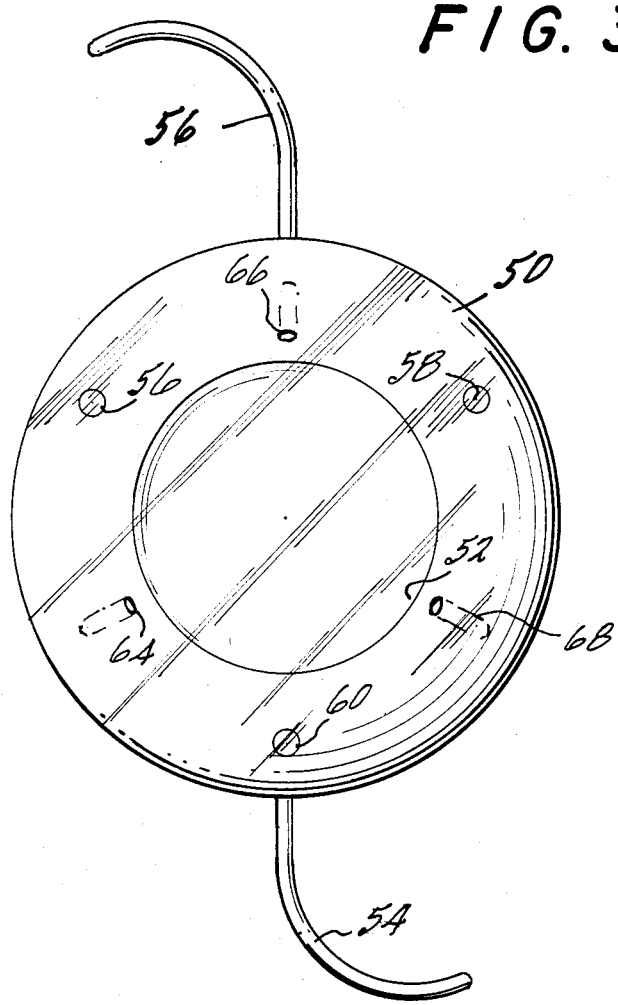
FIG. 3 shows a front view of a second embodiment of the present invention in which the protrusions are fixed in bore holes drilled into the lens body.
Figure 4:
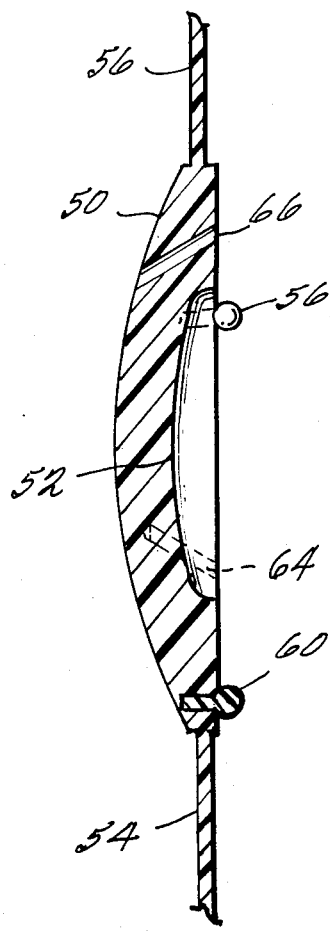
FIG. 4 shows a side elevation view of the lens of FIG. 3.
Figure 5:
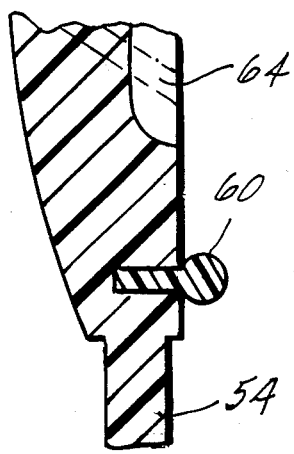
FIG. 5 shows a detailed view illustrating a protrusion fixed in a bore hole.

Reference is now made to FIGS. 3-5 which illustrate a second embodiment of the present invention. In this embodiment the protuberances are fixed in bore holes drilled in the lens body 50 about the central optical portion 52. As in the first embodiment integral appendages 54 and 56 extend from lens body 50 for fixing and mounting the lens within the posterior capsule. Three protrusions 56, 58 and 60 are illustrated in FIGS. 3-5 about the periphery of optical portion 52.

One of the advantages of this embodiment is that the lens can be easily configured to any desired number of protrusions. As shown in FIG. 3 additional bore holes 64, 66 and 68 are drilled about the optical portion in the lens body and can each be filled or not filled with a protuberance as desired. A second advantage of this arrangement is that the protuberances can be made of a material different from that of the lens body for example, a material which is softer and more friendly to the posterior capsule even further minimizing abrasion and possible damage. Materials which are less likely to be marked by the YAG laser in the event of misfocusing can also be employed. Suitable softer materials for use as protrusions include silicone and hydrogels, especially a hydrolphillic polymer containing a major amount of 2-hydroxyethyl methacrylate (HEMA). It is preferred that the polymer form a three dimensional cross-linked network. Polymethylmethacrylate, the preferred material of choice for the lens body, can also be used for the protuberances.

FIGS. 6-8 show a modification of the second embodiment of the present invention in which a ring 70 of suitable material includes a plurality of four protrusions 72, 74, 76 and 78 and is anchored to the posterior or rear surface of the lens body 80 for example by feet fixed within suitably drilled bore holes. As shown in FIG. 7, feet 86 and 88 of ring 70 are fixed in bore holes 90 and 92. Bore holes 94 and 96 are conventionally provided extending into the anterior or front surface of lens body 80 for use in insertion of the lens.

Many changes and modifications in the above described embodiment of the invention can of course be carried out without departing from the scope thereof. Accordingly that scope is intended to be limited only by the scope of the appended claims.

What is claimed is:

1. A posterior chamber intra-ocular lens for implantation in the eye comprising:

a lens body having a central optical portion and an anterior and posterior surface; and a ring detachably fixed to the posterior surface of said lens body to extend about said central optical portion and having a plurality of separated and unconnected protrusions extending outwardly and rearwardly from said ring to contact the posterior capsule without puncturing the posterior capsule and space the capsule from the rest of said lens body and to permit fluid circulation between the rear surface of said central optic and the posterior capsule.

2. A lens as in claim 1 further including centering means forming appendages integral with said lens body.

3. A lens as in claim 2 wherein said appendages are haptic loops.

4. A lens as in claim 1 wherein said protrusions each extend outwardly between 0.1 and 1 mm.

5. A lens as in claim 4 wherein said protrusions extend outwardly between 0.2 and 0.5 mm.

6. A lens as in claim 1 wherein said central optical portion and said protrusions are formed of different material.

7. A lens as in claim 1 wherein said protrusions are of material softer and more flexible than the material of said central optical portion.

8. A lens as in claim 7 wherein said protrusions are formed of a hydrogel.

9. A lens as in claim 8 wherein said hydrogel is a hydrophillic polymer.

10. A lens as in claim 1 wherein said protrusions are of silicone.

11. A lens as in claim 1 wherein said lens body is plastic.

12. A lens as in claim 11 wherein said plastic is polymethyl methacrylate.

13. A lens as in claim 1 further including centering means forming integral and flexible extensions of said lens body in a direction substantially transverse to the direction in which said protrusions extend.

14. A lens as in claim 13 wherein said centering means and lens body are of plastic.

15. A lens as in claim 14 wherein said plastic is polymethyl methacrylate.

* * * * *